United States Patent
Goto et al.

(10) Patent No.: US 7,639,879 B2
(45) Date of Patent: Dec. 29, 2009

(54) GROUP INFORMATION GENERATING SYSTEM AND GROUP INFORMATION GENERATING METHOD

(75) Inventors: Akira Goto, Otawara (JP); Kenichi Niwa, Otawara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 699 days.

(21) Appl. No.: 11/139,491

(22) Filed: May 31, 2005

(65) Prior Publication Data
US 2005/0267349 A1 Dec. 1, 2005

(30) Foreign Application Priority Data
May 31, 2004 (JP) .............................. 2004-162368

(51) Int. Cl.
G06K 9/62 (2006.01)

(52) U.S. Cl. ........................ 382/224; 382/132; 382/173; 382/261

(58) Field of Classification Search ................. 600/407, 600/476, 472, 437; 378/98.12, 98.6, 19; 382/261, 132, 130, 173, 294, 131; 73/606, 73/602, 620, 626; 324/309; 348/163, E5.089, 348/62; 708/308; 707/E17.009
See application file for complete search history.

(56) References Cited

U.S. PATENT DOCUMENTS

| | | | | | |
|---|---|---|---|---|---|
| 4,507,681 | A | * | 3/1985 | Verhoeven et al. | 378/98.7 |
| 4,672,651 | A | * | 6/1987 | Horiba et al. | 378/62 |
| 4,977,504 | A | * | 12/1990 | Funahashi | 382/132 |
| 5,588,071 | A | * | 12/1996 | Schultz | 382/168 |
| 5,594,807 | A | * | 1/1997 | Liu | 382/128 |
| 6,366,684 | B1 | * | 4/2002 | Gerard et al. | 382/132 |
| 7,203,354 | B2 | * | 4/2007 | Wilson et al. | 382/131 |

FOREIGN PATENT DOCUMENTS

JP 2004-337347 12/2004

* cited by examiner

*Primary Examiner*—Sheela C Chawan
(74) *Attorney, Agent, or Firm*—Oblon, Spivak, McClelland, Maier & Neustadt, L.L.P.

(57) ABSTRACT

A group information generating system 1 comprises a group border information generating units 9 or 10 and a group information generating unit 12. The group border information generating unit 9 or 10 is configured to generate a border information indicating at least one border of group when medical images sorted into the group are to be indicated according to an information included in a medical image information. The group information generating unit 12 is configured to generate a group information according to the border information. The group information means a discernment information of the group to which an image indicating information included in the medical image information for indicating one of the medical images is belong.

18 Claims, 11 Drawing Sheets

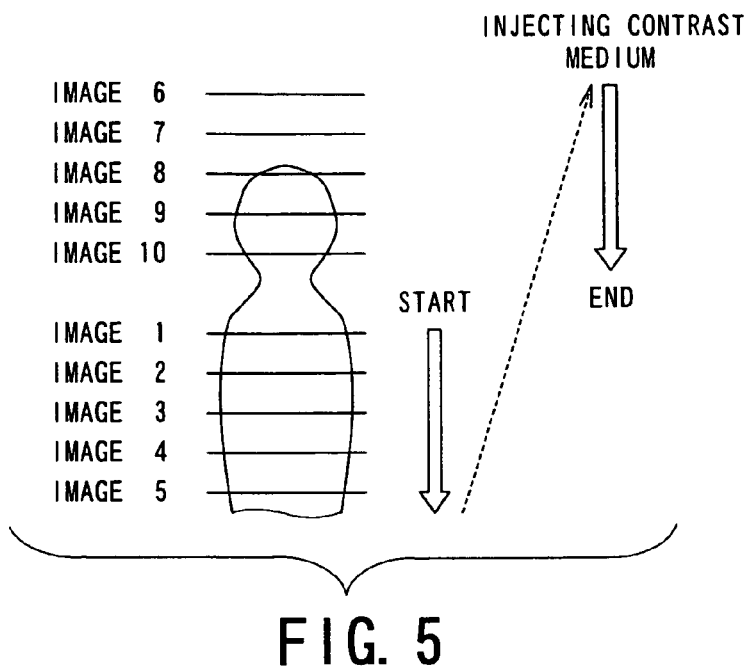
FIG. 5
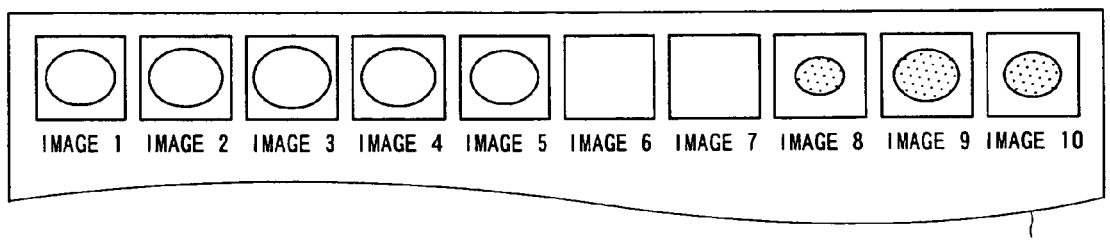
FIG. 6
|  | X | Y | Z |  |  |
|---|---|---|---|---|---|
| IMAGE 1 | −175 | −175 | −1514.02 | | |
| IMAGE 2 | −175 | −175 | −1524.02 | | |
| IMAGE 3 | −175 | −175 | −1534.02 | | |
| IMAGE 4 | −175 | −175 | −1544.02 | | A(, A') |
| IMAGE 5 | −175 | −175 | −1554.02 | ↑ GR1 | |
| IMAGE 6 | −175.781 | −175.7812 | −1084.02 | ↓ GR2 | |
| IMAGE 7 | −175.781 | −175.7812 | −1094.02 | | |
| IMAGE 8 | −175.781 | −175.7812 | −1104.02 | | A' |
| IMAGE 9 | −175.781 | −175.7812 | −1114.02 | | |
| IMAGE 10 | −175.781 | −175.7812 | −1124.02 | | |
FIG. 7

[CT IMAGE USE]

| TAG | VR | NAME |
|---|---|---|
| 0018, 0010 | LO | Contrast/Bolus Agent |
| 0018, 0015 | CS | Body Part Examined |
| 0018, 0050 | DS | Slice Thickness |
| 0018, 0060 | DS | KVP |
| 0018, 1042 | TM | Contrast/Bolus Start Time |
| 0018, 1151 | IS | X-ray Tube Current |
| 0018, 1152 | IS | Exposure |
| 0018, 1210 | SH | Convolution Kernel |
| 0020, 0011 | IS | Series Number |
| 0020, 0032 | DS | Image Position(Patient) |

FIG. 20

[MR IMAGE USE]

| TAG | VR | NAME |
|---|---|---|
| 0018, 0010 | LO | Contrast/Bolus Agent |
| 0018, 0015 | CS | Body Part Examined |
| 0018, 0050 | DS | Slice Thickness |
| 0018, 0080 | DS | Repetition Time |
| 0018, 0081 | DS | Echo Time |
| 0018, 0082 | DS | Inversion Time |
| 0018, 0086 | IS | Echo Number(s) |
| 0020, 000e | UI | Series Instansce UID |
| 0020, 0012 | IS | Acquisition Number |
| 0020, 0032 | DS | Image Position(Patient) |

FIG. 21

GROUP INFORMATION GENERATING SYSTEM AND GROUP INFORMATION GENERATING METHOD

BACKGROUND OF THE INVENTION

1. Field of the Invention

The present invention relates to a group information generating system and a group information generating method that generate group informations for indicating medical images obtained by modalities with grouping the medical images to some groups.

2. Description of the Related Art

Typically, medical images obtained by medical imaging apparatuses (modalities), such as MRI (magnetic resonance imaging) apparatuses and X-ray CT (computed tomography) apparatuses, are grouped for each group, such as a patient, a modality, examination date-and-time, or an examination type. When multiple medical images are displayed on a medical-image referring apparatus, medical images belonging to the same group are displayed in an aligned manner.

In such a manner, the grouped medical images are associated with group information for identifying the corresponding group and are managed in an identifiable manner. In particular, some recent modalities have functions for automatically generating group information based on information, such as imaging time, and associating the group information with medical images. The group information is added to medical images obtained by such modalities.

For example, when medical image data is generated according to DICOM (Digital Imaging and Communications in Medicine) known as a typical standard for medical image data, series information for grouping medical image data into a group called a series is added to the medical image data.

The medical images to which the series information is added is supplied, as medical image information, to a medical-image referring apparatus, on which the medical images are then displayed in an aligned manner for each series in accordance with the series information. Thus, when a modality having a function for generating the series information is used, medical images can be sorted into groups that are more suitable for diagnosis and be displayed on a medical image referring apparatus in an aligned manner, without being additionally separated into groups.

With respect to medical images obtained by a known modality that lacks a function for sorting medical images into groups, a user may sort the medical images into groups in accordance with information, such as imaging time and a modality, so as to allow the medical images to be displayed on a medical image referring apparatus for each group in accordance with group information added by the user.

An image filing apparatus is proposed as a technology for grouping and organizing multiple image files (see, for example, JP-A-2001-333352). Specifically, the image filing apparatus sorts image files, recorded on multiple storage media for imaging, into groups in accordance with a difference in continuity of use between the storage media.

However, when a known medical image referring apparatus is used to display multiple medical images, the medical images are displayed as being sorted into unintended groups or medical images to be sorted into a group are displayed without being appropriately sorted into the group in some cases.

The main cause is that the grouping of medical images is determined based on only group information contained in medical image information when the medical images are displayed on the medical image referring apparatus. That is, when a method for generating group information is different for each manufacturer or version of a modality and the type of group information recognized by a medical image referring apparatus and the type of group information generated by the modality are different from each other, the medical image referring apparatus cannot appropriately recognize the group information, so that the medical images are displayed without being sorted into groups.

In particular, group information generated by a known modality is not appropriately recognized by a medical image referring apparatus in many cases and, for example, all of multiple medical images obtained by a known modality may be sorted into different groups.

As another example, when tomographic images of the entire body of a subject are obtained before and after a contrast medium is injected, in some cases, scanning is executed from the subject's head side toward the foot side before injection of the contrast medium and scanning is sequentially performed from the subject's foot side toward the head side after injection of the contrast medium so as to reduce imaging time. In such a case, it is essentially desired that the subject's tomographic images obtained by the scanning before injection of the contrast medium and the subject's tomographic images obtained by the scanning after injection of the contrast medium are divided into different groups for display.

However, since the scanning after injection of the contrast medium is sequentially executed, the subject's tomographic images obtained both before and after injection of the contrast medium are sorted into one group in some cases. As a result, the tomographic images obtained before and after injection of the contrast medium are not appropriately sorted into groups, and thus all the tomographic images are displayed on the medical image referring apparatus in an aligned manner.

When such medical images that are displayed without being appropriately sorted into groups are used for diagnosis, a large amount of time and effort is required for interpreting the medical images. In some cases, the flow of imaging the medical images cannot be understood, thereby making it difficult to perform three-dimensional interpretation on the subject.

Accordingly, in order to prevent such problems, it is desired to develop a technology for, without a user's work, automatically generating group information for appropriately displaying medical images on a medical image referring apparatus for each group regardless of the type of group information generated for each modality.

SUMMARY OF THE INVENTION

Accordingly, the present invention has been made in light of the conventional situations, and it is an object of the present invention to provide a group information generating system and a group information generating method that make it possible to generate group informations automatically for indicating medical images obtained by modalities with grouping the medical images to some groups appropriately.

In an aspect, to achieve the object, the present invention provides a group information generating system comprising a group border information generating unit configured to generate a border information indicating at least one border of group when medical images sorted into the group are to be indicated according to an information included in a medical image information and a group information generating unit configured to generate a group information according to the border information, the group information meaning a discernment information of the group to which an image indicating information included in the medical image information for indicating one of the medical images is belong.

Furthermore, in an aspect, to achieve the object, the present invention provides a group information generating method comprising generating a border information indicating at least one border of group when medical images sorted into the group are to be indicated according to an information included in a medical image information and generating a group information according to the border information, the group information meaning a discernment information of the group to which an image indicating information included in the medical image information for indicating one of the medical images is belong.

In the group information generating system and the group information generating method as described above, it is possible to generate group informations automatically for indicating medical images obtained by modalities with grouping the medical images to some groups appropriately.

BRIEF DESCRIPTION OF THE DRAWINGS

In the accompanying drawings:

FIG. 5 is a diagram showing an example of cross sections of an object for imaging with a modality using the way of go and go type to move the bed after or before injecting contrast medium;

FIG. 6 is a diagram showing an example of cross section images of each cross section of the object shown in FIG. 5 lined up and indicated according to the medical image informations read into the group information generating system shown in FIG. 1;

FIG. 7 is a diagram explaining an example of the way to generate border informations of the groups by showing the time-lined position informations of the bed which are in the incidental informations included in the medical image informations;

FIG. 20 is a table indicating an example of a part of tags for CT images, which can be used for generating group-border information and descriptions of them in the incidental information of the medical image information shown in FIG. 19; and FIG. 21 is a table indicating an example of a part of tags for MR images, which can be used for generating group-border information and descriptions of them in the incidental information of the medical image information shown in FIG. 19.

DESCRIPTION OF THE PREFERRED EMBODIMENTS

A group information generating system and a group information generating method according to embodiments of the present invention will be described with reference to the accompanying drawings.

Figure 1:
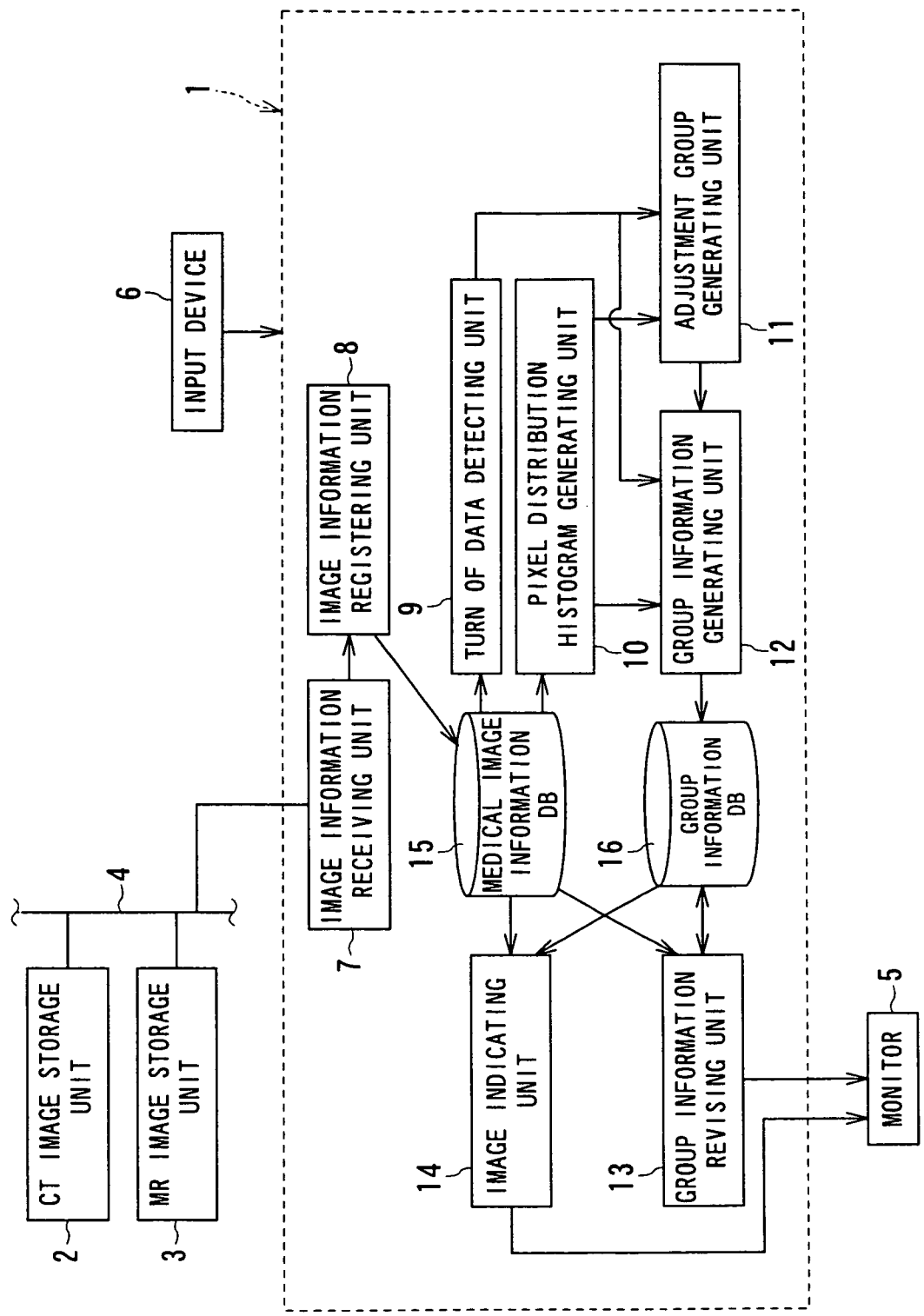
FIG. 1 is a functional block diagram showing an embodiment of a group information generating system according to the present invention.

FIG. 1 is a functional block diagram showing an embodiment of a group information generating system according to the present invention.

A group information generating system 1 is connected to some medical image storage units such as a CT image storage unit 2 and a MR (magnetic resonance) image storage unit 3 with a network. The CT image storage unit 2 and the MR image storage unit 3 store medical image informations such as CT image informations and MR image informations of objects previously imaged with modalities such as X-ray CT apparatus and MRI apparatus (neither of them is shown). The medical image information stored in the CT image storage unit 2 or the MR image storage unit 3 includes an incidental information having some informations such as the position information of the bed and the date and time information on imaging the medical image as well as an image indicating information having values of pixels, color information and so on for indicating the medical image.

The group information generating system 1 is a system including a computer which operates as an image information receiving unit 7, an image information registering unit 8, a turn of data detecting unit 9 as an example of a group border information generating unit, a pixel distribution histogram generating unit 10 as an example of a group border information generating unit, an adjustment group generating unit 11, a group information generating unit 12, a group information revising unit 13, an image indicating unit 14, a medical image information database 15 and a group information database 16 by inputting a group information generating program to the computer having a monitor 5, an input device 6, not shown storage unit and not shown operating unit.

A group-information generating system 1, which includes these elements, allows medical images to be displayed on a monitor 5 in accordance with medical image information stored on the CT image storage unit 2 and the MR image storage unit 3. For the display, the group-information generating system 1 is configured so as to generate group information for sorting the individual medical images into groups and displaying the medical images for each group, that is, discernment information for a group to which each piece of image-indicating information belongs, so that the multiple medical images can be displayed on the monitor 5 in an aligned manner for each group in accordance with the generated group information, according to need.

When the medical image information is generated based on DICOM, which is a typical standard for medical image information, series information for displaying medical images in series has been added to the medical image information stored in the CT image storage unit 2 or the MR image storage unit 3. Thus, a group generated by the group-information generating system 1 can be referred to as one type of local series, which is a series for further dividing a series depending on a user application.

The image information receiving unit 7 has a function for receiving the medical image information, such as CT image information and MR image information, from the CT image storage unit 2 and the MR image storage unit 3 and supplying the received medical image information to the image information registering unit 8. By writing the medical image information, received from the image information receiving unit 7, to the medical image information database 15, the image information registering unit 8 has a function for registering the medical image information into the group-information generating system 1, as information to be sorted into groups.

The turn of data detecting unit 9 has a function for obtaining incidental information, such as position information of the bed and date-and-time information, that is contained in the medical image information stored in the medical image information database 15, in response to an instruction from an input device 6. The turn of data detecting unit 9 further has a function for generating border information, which indicates a border portion for different groups, in accordance with the obtained incidental information and supplying the border information to the adjustment group generating unit 11 or the group information generating unit 12.

The pixel distribution histogram generating unit 10 has a function for generating a pixel distribution histogram from the medical image information stored in the medical image information database 15 in response to an instruction from the input device 6, generating border information for groups in accordance with the generated pixel distribution histogram, and supplying the border information to the adjustment group generating unit 11 or the group information generating unit 12. The pixel distribution histogram indicates the frequencies of pixels whose pixel values exceed a predetermined threshold in an arbitrary direction of each medical image.

The adjustment group generating unit 11 has a function for generating multiple pieces of group border information as adjustment group border information in order to generate a group for adjustment, by using a predetermined arbitrary method, from a single piece of group border information, in accordance with the group border information received from the turn of data detecting unit 9 or the pixel distribution histogram generating unit 10. The adjustment group generating unit 11 further has a function for supplying the generated adjustment group border information to the group information generating unit 12.

The group information generating unit 12 has a function for generating group information in accordance with the group border information received from the turn of data detecting unit 9 or the pixel distribution histogram generating unit 10 and the adjustment group border information received from the adjustment group generating unit 11 and a function for writing the generated group information to the group information database 16.

The group information revising unit 13 has a function for displaying arbitrary images for reference, which images are associated with medical images to be used for grouping, in accordance with the medical image information read from the medical image information database 15. Examples of the images for reference include scanogram images, 3-dimmensional axial data, 3-dimmensional coronal data, and 3-dimmensional sagittal data. The group information revising unit 13 further has a function for reading the group information stored in the group information database 16 and causing a group border to be displayed on the monitor 5 together with the images for reference, and a function for revising the group information read from the group information database 16 and writing the revised group information to the group information database 16 in accordance with information received from the input device 6.

The image indicating unit 14 has a function for reading information other than the group information, such as image-indicating information, of the medical image information stored in the medical image information database 15, and group information stored in the group information database 16, and for supplying the image-indicating information to the monitor 5 in accordance with the read group information, so that multiple medical images are displayed in an aligned manner for each group.

Next, the operation of the group information generating system 1 will be described.

First, various modalities, such as an MRI and an X-ray CT apparatus (not shown), collect medical image information for displaying multiple images of a subject. For example, a contrast medium is injected to a subject set on a bed (not shown) and, after and before the injection of the contrast medium, the modalities collect medical image information for tomographic images of each slice of the subject while the bed is moved.

Figure 2:
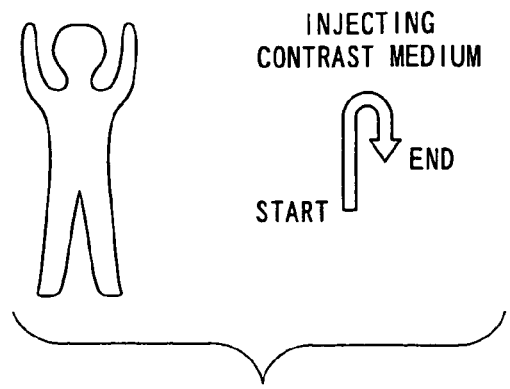
FIG. 2 is a diagram explaining the way of go and reverse type to move the bed on imaging contrast images of an object by various modalities with injecting contrast medium to the object.
Figure 3:
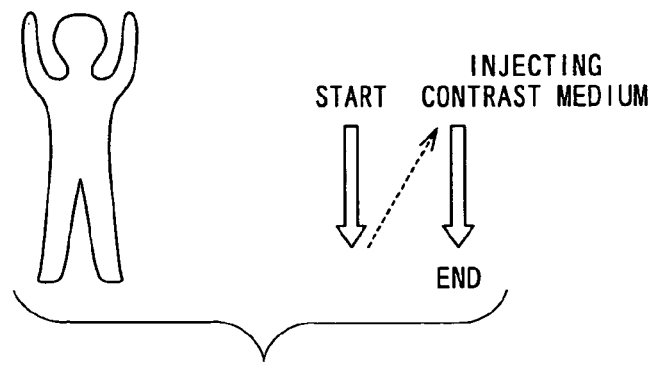
FIG. 3 is a diagram explaining the way of go and go type to move the bed on imaging contrast images of an object by various modalities with injecting contrast medium to the object.

FIG. 2 is a diagram explaining the way of go and reverse type to move the bed on imaging contrast images of an object by various modalities with injecting contrast medium to the object. FIG. 3 is a diagram explaining the way of go and go type to move the bed on imaging contrast images of an object by various modalities with injecting contrast medium to the object.

As shown in FIG. 2, when contrast images of a subject are imaged by go-and-reverse type of bed moving method, for example, the bed is moved in the negative direction of the body axis before the contrast medium is injected to the subject and the entire body or a part thereof are imaged from the subject's foot side toward the head side. After the contrast medium is injected to the subject, the bed is moved in the positive direction of the body axis and the entire body or a part thereof are imaged from the subject's head side toward the foot side. That is, the bed-moving directions before and after the contrast medium injection are opposite to each other.

In contrast, as shown in FIG. 3, when contrast images of a subject are imaged by a go-and-go type of bed moving method, for example, the bed is moved in the positive direction of the body axis before the contrast medium is injected to the subject and the entire body or a part thereof are imaged from the subject's head side toward the foot side. After the contrast medium is injected to the subject, the bed is also moved in the positive direction of the body axis and the entire body or a part thereof are imaged from the subject's head side toward the foot side. That is, the bed moving directions before and after the contrast medium injection are the same.

As such bed moving method, either the go-and-reverse type or the go-and-go type is selected depending on the purpose of diagnosis.

For example, when the modality is an X-ray CT apparatus, medical image information for X-ray contrast CT images is sent to and stored in the CT image storage unit 2 via a network 4. When the modality is not connected to the network 4, medical image information is input to the CT image storage unit 2 and/or the MR image storage unit 3 via an information storage medium and is stored.

Thereafter, information that is referred to when medical images to be displayed are sorted into groups is selected in advance. That is, in the group-information generating system 1, the turn of data detecting unit 9 can sort medical images into groups in accordance with incidental information, such as position information of the bed and date-and-time information, that is contained in the medical image information, and the pixel distribution histogram generating unit 10 can also sort medical images into groups in accordance with the image distribution histogram that the pixel distribution histogram generating unit 10 creates based on the medical image information. Thus, selection information about method for generating the group information is input to the input device 6, and a method for generating the group information is selected. For example, the method for generating the group information is selected in accordance with, for example, the position information of the bed.

Figure 4:
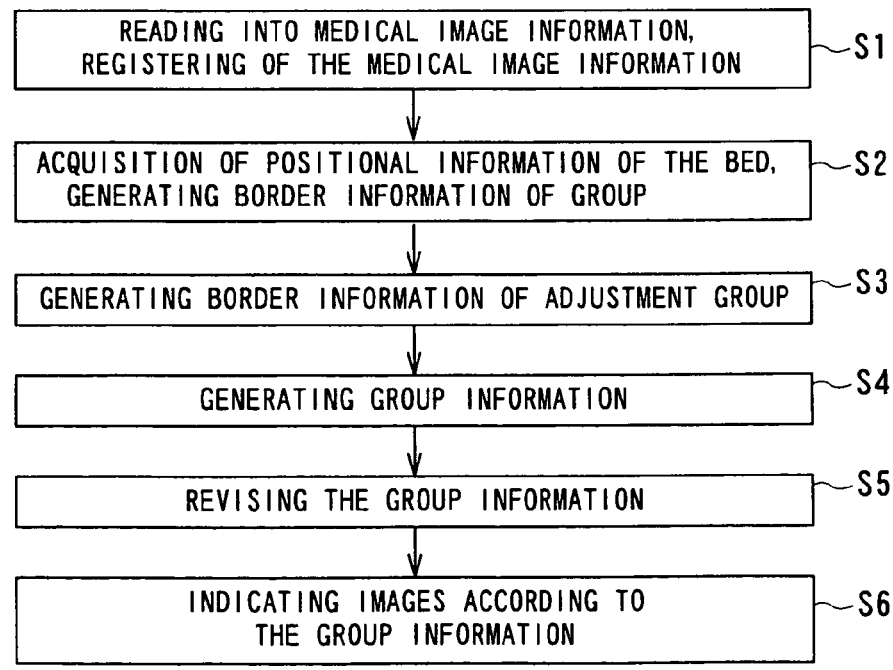
FIG. 4 is a flowchart showing an example of flow for indicating medical images sorted into the groups on the monitor according to the position information of the bed by the group information generating system shown in FIG. 1.

FIG. 4 is a flowchart showing an example of flow for indicating medical images sorted into the groups on the monitor 5 according to the position information of the bed by the group information generating system 1 shown in FIG. 1. The symbols including S with a number in FIG. 4 indicate each step of the flowchart.

First, in step S1, medical image information for medical images to be displayed is read and registered by the group-information generating system 1. That is, instruction information for reading medical image information is input from the input device 6 and is supplied to the image information receiving unit 7. In accordance with the information received from the input device 6, the image information receiving unit 7 reads medical image information, such as CT image information supplied from the CT image storage unit 2 or MR image information supplied from the MR image storage unit 3, via the network 4. In addition, the image information receiving unit 7 supplies the medical image information, read from the CT image storage unit 2 or the MR image storage unit 3, to the image information registering unit 8. The image information registering unit 8 then writes the medical image information, received from the image information receiving unit 7, to the medical image information database 15, so that the group-information generating system 1 registers the medical image information.

FIG. 5 is a diagram showing an example of cross sections of an object for imaging with a modality using the way of go and go type to move the bed after or before injecting contrast medium. FIG. 6 is a diagram showing an example of cross section images of each cross section of the object shown in FIG. 5 lined up and indicated according to the medical image informations read into the group information generating system 1 shown in FIG. 1.

As shown in FIG. 5, when the medical image information is for a subject's slice tomographic image obtained before and after the contrast medium injection by using the go-and-go type of bed moving method, the bed moving directions after and before the contrast medium injection are the same. Thus, when the tomographic images are time-sequentially displayed on the monitor 5 in the order of imaging time in accordance with the time information of the incidental information contained in the medical image information, images as shown in FIG. 6 are displayed.

Specifically, for example, when a total number of ten tomographic images of the entire body of a subject exist with five tomographic images obtained before the contrast medium injection and five tomographic images obtained after the contrast medium injection, the ten tomographic images (image 1, image 2, . . . , image 10) are displayed on the monitor 5 in an aligned manner in a time series. That is, as shown in FIG. 6, five tomographic images (image 1, image 2, . . . , image 5) obtained before the contrast medium injection are first displayed in an aligned manner and five tomographic images (image 6, image 7, . . . , image 10) obtained after the contrast medium injection are then displayed in an aligned manner.

The five tomographic images (image 1, image 2, . . . , image 5) before the contrast medium injection are imaged, for example, from the positive side of the body-axis toward the negative side with respect to the body trunk of the subject and their shape changes gradually. On other hand, the five tomographic images (image 6, image 2, . . . , image 10) after the contrast medium injection are imaged from the positive side of the body-axis toward the negative side with respect to the head portion, and the first two tomographic images (image 6, image 7) correspond to the outside of the subject and thus have no figure and the other three tomographic images (image 8, image 9, image 10) have figures of the subject's cross-section enhanced with a contrast medium.

In such a case, however, for diagnosis, it is desired that the subject's tomographic images obtained before the contrast medium injection and the subject's tomographic images obtained after the contrast medium injection be sorted into respective different groups and be displayed on the monitor 5 for each group. Accordingly, incidental information contained in the medical image information is extracted in order to generate the group information.

In step S2, the turn of data detecting unit 9 reads the medical image information stored in the medical image information database 15 and acquires the incidental information, such as position information of the bed and date-and-time information, that is contained in the medical image information. The turn of data detecting unit 9 then generates group border information in accordance with the acquired incidental information.

FIG. 7 is a diagram explaining an example of the way to generate border informations of the groups by showing the time-lined position informations of the bed which are in the incidental informations included in the medical image informations.

The incidental information, such as time information and position information of the bed, is added to information that is used for displaying each image and that is included in the medical image information. FIG. 7 shows the positions of the bed when the tomographic images (image 1, image 2, ..., image 10) shown in FIG. 6 are imaged are arranged in a time series in XYZ coordinates. As shown in FIG. 7, the X coordinates and the Y coordinates for the first five tomographic images (image 1, image 2, ..., image 5) before the contrast medium injection are constant and the Z coordinates, which represent the body axis direction of the subject, decrease at a constant rate. Thus, while the first five tomographic images (image 1, image 2, ..., image 5) are imaged, it can be understood that the bed is moved in the positive direction of the body axis, i.e., from the subject's foot side toward the head side.

The X coordinate and the Y coordinate of the fifth tomographic image (image 5) are slightly different from the X coordinate and the Y coordinate of the sixth tomographic image (image 6) and the Z coordinate increases significantly. Further, the X coordinates and the Y coordinates of the sixth and subsequent tomographic images (image 6, image 2, ..., image 10) are constant and the Z coordinates decrease at a constant rate. Therefore, it is possible to determine from only the position information of the bed that the bed turns back, moves greatly from the subject's head side toward the foot side, and moves gradually from the subject's foot side toward the head side again after the imaging of the fifth tomographic image (image 5) is completed, without referring to each tomographic image (image 1, image 2, ..., image 10).

Thus, for the information for the ten tomographic images (image 1, image 2, ..., image 10) having the incidental information shown in FIG. 7, it can be understood on the position information of the bed that it is desired that a group border A be set between the first five tomographic images (image 1, image 2, ..., image 5) and the sixth and subsequent tomographic images so (image 6, image 7, ..., image 10) that the first five tomographic images and the sixth and subsequent tomographic images are sorted into different groups for display.

Accordingly, the turn of data detecting unit 9 calculates a difference in the position information of the bed of the incidental information, with respect to each tomographic image (image 1, image 2, ..., image 10). When the calculated difference value is extremely larger than another difference value, for example, when a difference between a difference value and another difference value exceeds a preset threshold, it is determined that the bed turns back at a point corresponding to the difference value and group border information is generated so that the tomographic images (image 1, image 2, ..., image 10) are sorted into different groups. The generated group border information is supplied to the adjustment group generating unit 11 or the group information generating unit 12.

The method for generating the group border information is based on whether or not a difference between the difference values of the incidental information, such as the position information of the bed, exceeds a preset threshold as described above. Alternatively, when the incidental information itself is within a preset range, tomographic images corresponding to the incidental information can be sorted into the same group. For example, the group border information can be generated so that, when the value in the incidental information (e.g., the position information of the bed) is 0 to 500, corresponding tomographic images are sorted into group 1 and, when the value is 500 to 1000, corresponding tomographic images are sorted into group 2.

That is, the turn of data detecting unit 9 sets the group border A between the fifth tomographic image (image 5) and the sixth tomographic image (image 6) so that, as shown in FIG. 7, the first five tomographic images (image 1, image 2, ..., image 5) are sorted into group 1 (GR1) and the sixth and subsequent tomographic images (image 6, image 7, ..., image 10) are sorted into group 2 (GR2), and supplies the group border A to the adjustment group generating unit 11 or the group information generating unit 12 as a group border information.

As shown in FIG. 6, in practice, the tomographic images (image 1, image 2, ..., image 10) may include images that are unnecessary for diagnosis, such as images of the outside of the subject. For example, in FIG. 6, it is desired that two images (image 6, image 7) obtained after the contrast medium injection be excluded from the group, since they are images of the outside of the subject and thus are not tomographic images of the subject. When the group border information is generated with reference to only the position information of the bed, it is difficult to determine whether or not the tomographic images in question correspond to the outside of the subject. Thus, a need for adjusting the group border A arises.

In step S3, when the group border A needs to be adjusted as described above, the group border information is supplied to the adjustment group generating unit 11, which, in turn, sets borders A' for creating an adjustment group to generate adjustment group border information. Using a predetermined method, the adjustment group generating unit 11 generates multiple pieces of adjustment group border information from a single piece of group border information.

For example, with reference to the group border A received from the turn of data detecting unit 9, the adjustment group generating unit 11 generates adjustment group border information so that the first two tomographic images of group 2 (GR2) side are sorted into an adjustment group. That is, as shown in FIG. 7, the adjustment group generating unit 11 designates the group border A, received from the turn of data detecting unit 9, as one border A' of the adjustment group and also sets another border A' thereof between the seventh tomographic image (image 7) and the eighth tomographic image (image 8), and supplies the borders A' to the group information generating unit 12 as adjustment group border information.

The boarders A' for the adjustment group may be set so as to have margins for both group 1 (GR1) side and group 2 (GR2) side from the group border A received from the turn of data detecting unit 9. Furthermore, the adjustment group border information may be generated so that two or more adjustment groups are generated. In addition, the method for creating the adjustment group is not limited to a method for determining the adjustment group borders A' from the number of data and the position of the reference group-border A received from the turn of data detecting unit 9. For example, the adjustment group may be set by referring to the position information of the bed and comparing it with a preset threshold.

Next, in step S4, the group information generating unit 12 generates group information in accordance with the group border information and the adjustment group border information received from the turn of data detecting unit 9 or the adjustment group generating unit 11. That is, when an adjustment group is created, the adjustment group border information received from the adjustment group generating unit 11, in addition to the group border information received from the turn of data detecting unit 9, is used to generate group information. When an adjustment group is not created, only the group border information received from the turn of data detecting unit 9 is used to generate group information.

The group information generating unit 12 generates group information that indicates a group to which medical images to be sorted into the same group belong, from the adjustment group border information and the group border information, and writes the generated group information to the group information database 16. In this case, the group information generating unit 12 sets, in the group information, the display order of medical images to be sorted into the same group, according to need. In the case of the medical images shown in FIG. 6, since the bed moving directions before and after the contrast medium injection are the same, the group information generating unit 12 sets the display order of the medical images to, for example, the time-sequence order.

Figure 8:
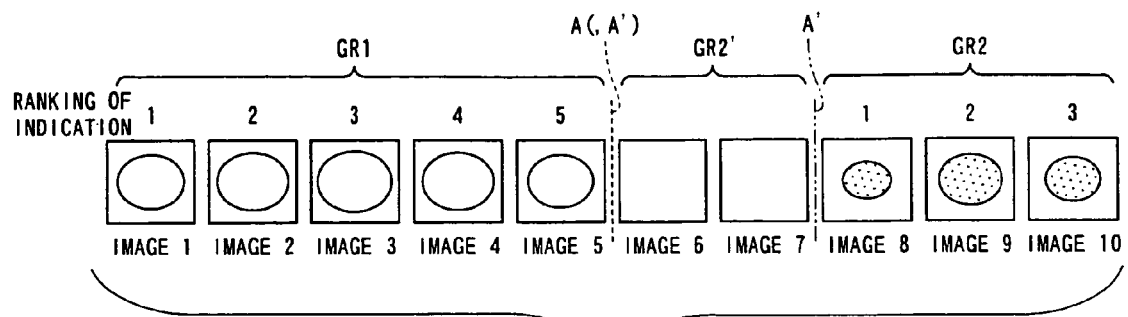
FIG. 8 is a diagram indicating a concept of the group informations related to cross section images of the object shown in FIG. 6.
Figure 9:
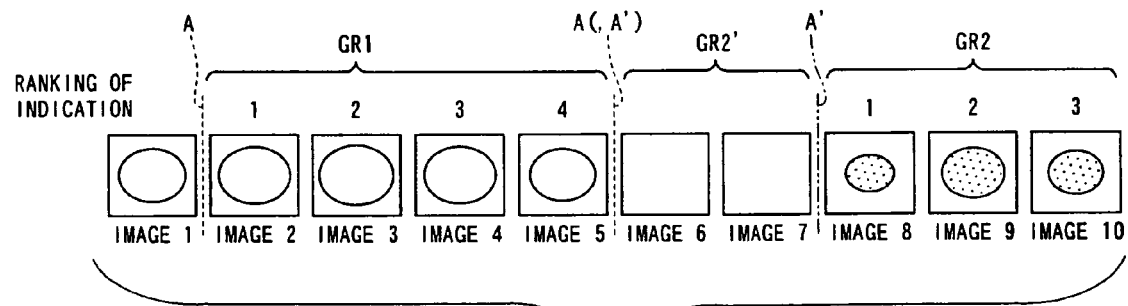
FIG. 9 is a diagram indicating a concept of the revised group informations related to cross section images of the object shown in FIG. 6.

FIG. 8 is a diagram indicating a concept of the group informations related to cross section images of the object shown in FIG. 6. FIG. 9 is a diagram indicating a concept of the revised group informations related to cross section images of the object shown in FIG. 6.

As shown in FIG. 8, when ten tomographic images are arranged in a time series as in the case of FIG. 6, five tomographic images (image 1, image 2, . . . , image 5) that were imaged before the contrast medium injection and that are divided by the group border A (the adjustment group border A') are associated with group 1 (GR1). Two tomographic images (image 6, image 7) that were imaged after the contrast medium injection and that are divided by the adjustment group borders A' are associated with group 2' (GR2') and are excluded from images to be displayed. Additionally, the other three tomographic images (image 8, image 9, image 10) that were imaged after the contrast medium injection and that are divided by the adjustment group border A' are associated with group 2 (GR2).

Since the directions of bed moving during the imaging of the tomographic images (image 1, image 2, . . . , image 10) are the same, the ranking of indication of the images in each group is in a time series.

As described above, this arrangement makes it possible to display multiple medical images in a group in accordance with the group information stored in the group information database 16. In practice, however, the user needs to change the group borders arbitrarily in some cases.

Accordingly, in step S5, the group information revising unit 13 appropriately revises the group information stored in the group information database 16, as required. For this purpose, the group information revising unit 13 first reads information, contained in the medical image information, from the medical image information database 15 and supplies the read information to the monitor 5, so that the monitor 5 displays arbitrary images for reference which allows checking of the group borders A and A', together with the position of the tomographic images corresponding to the group information. The images for reference are, for example, scanogram images, 3D axial data, 3D coronal data, and 3D sagittal data. The group borders A and A' are displayed together with the images for reference.

Consequently, the user can understand the position of each tomographic image and image combinations for grouping. For example, in FIG. 8, when the first image (image 1) is not required for diagnosis, excluding information for displaying the first image (image 1) from group 1 (GR1) reduces the data size and is thus advantageous for the subsequent data management. Accordingly, by inputting information for designating the group borders A and A' through the input device 6, it is possible to adjust the image combinations for grouping while referring to the images for reference such as scanogram images.

Thus, the 13 receives the information for designating the group borders A and A' from the input device 6, and the group information revising unit 13 revises the group information stored in the group information database 16 in accordance with the received information. Consequently, as shown in FIG. 9, the border A of group 1 (GR1) is changed and image 1 is excluded from group 1 (GR1). The display order is also updated in response to the change in the group border A. Group information for displaying images in a group as intended by the user is stored in the group information database 16.

In step S6, the group information generated in that manner is supplied from the group information database 16 to the image indicating unit 14, and the image indicating unit 14 supplies the image-indicating information, read from the medical image information database 15, to the monitor 5 in accordance with the group information. Consequently, tomographic images of the subject are displayed in a group on the monitor 5 in an aligned manner.

Figure 10:
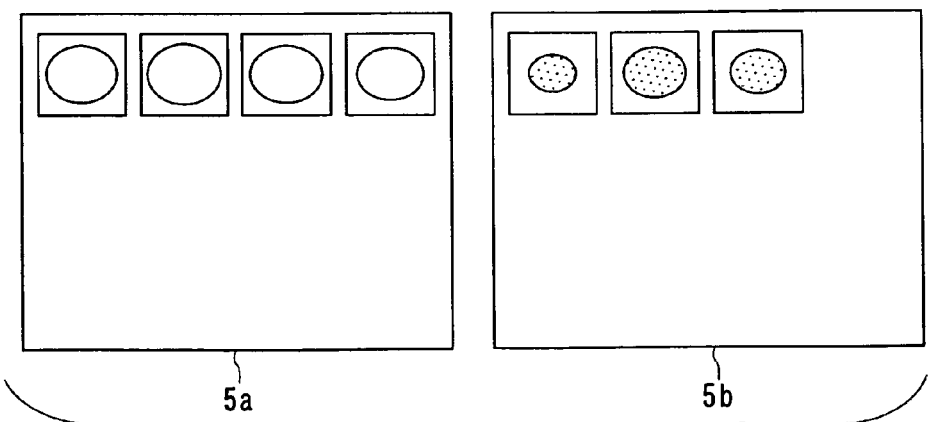
FIG. 10 is a diagram showing an example of the cross section images shown in FIG. 9 indicated on the monitor according to the group informations.

FIG. 10 is a diagram showing an example of the cross section images shown in FIG. 9 indicated on the monitor 5 according to the group informations.

As shown in FIG. 10, tomographic images are displayed for each group in accordance with the group information. That is, four tomographic images (image 1, image 2, image 3, image 4) sorted into group 1 (GR1) are displayed on a common monitor 5*a* and three tomographic images (image 8, image 9, image 10) sorted into group 2 (GR2) are displayed on another common monitor 5*b*.

On the other hand, the user can select a method for generating the group information, based on pixel distributions of medical image. In such a case, the user pre-enters information, indicating that the creation of the group information is started based on pixel distributions of the medical image, to the input device 6 in advance. Thus, a method for generating the group information based on pixel distributions of the medical image is selected.

Figure 11:
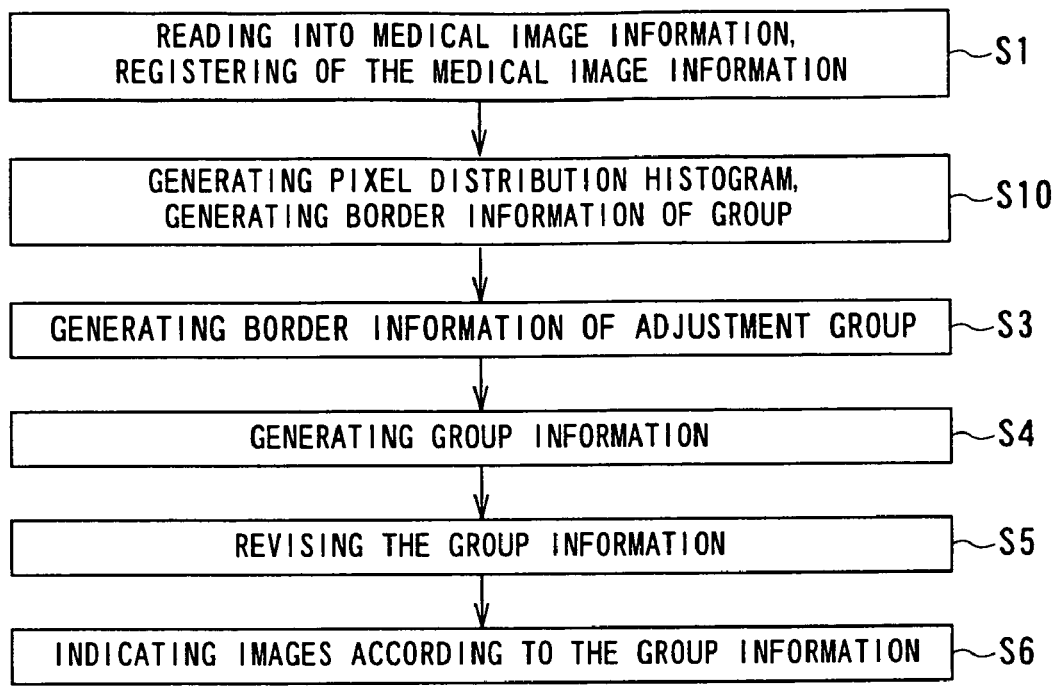
FIG. 11 is a flowchart showing an example of flow for indicating medical images sorted into the groups on the monitor according to the pixel distributions of the medical images by the group information generating system shown in FIG. 1.

FIG. 11 is a flowchart showing an example of flow for indicating medical images sorted into the groups on the monitor 5 according to the pixel distributions of the medical images by the group information generating system 1 shown in FIG. 1. The symbols including S with a number in FIG. 11 indicate each step of the flowchart. The same symbol to that in FIG. 4 is attached to each of the steps in FIG. 11 which are equivalent to the steps in FIG. 4 respectively, and explanation of those steps is omitted.

Fist, in step S1 shown in FIG. 11, medical image information is read by the image information receiving unit 7 and is written to the medical image information database 15 by the image information registering unit 8.

Next, in step S10, the pixel distribution histogram generating unit 10 generates a histogram for pixel distribution in an arbitrary direction of each medical image, based on the medical image information stored in the medical image information database 15, and sets a group border, based on the generated pixel distribution histogram.

Figure 12:
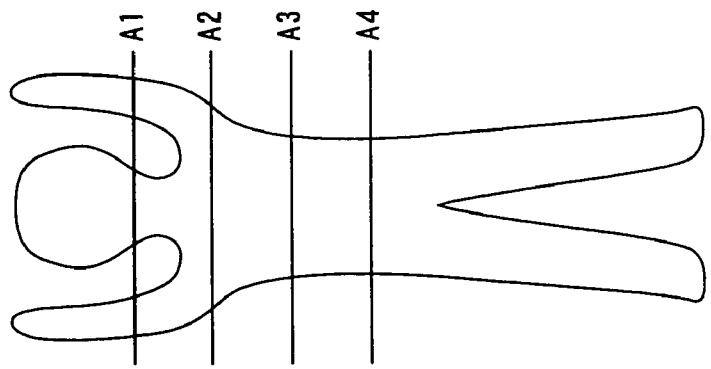
FIG. 12 is a diagram indicating an example of positions for cross sections of the object on accumulating the medical image informations stored in the medical image information database of the group information generating system shown in FIG. 1.

FIG. 12 is a diagram indicating an example of positions for cross sections of the object on accumulating the medical image informations stored in the medical image information database 15 of the group information generating system 1 shown in FIG. 1.

As shown in FIG. 12, tomographic images of the head and the body trunk of the subject whose both arms raised, along cross sections A1, A2, A3, and A4, which are perpendicular to the body axis are imaged for example.

Figure 13:
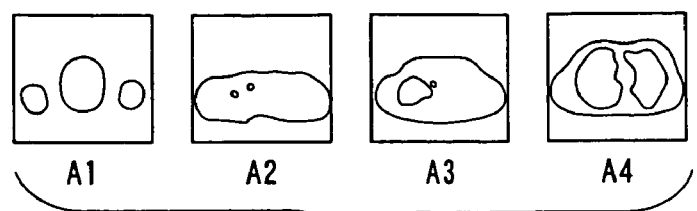
FIG. 13 is a diagram showing an example of the cross section images on the cross sections A1, A2, A3 and A4 of the object shown in FIG. 12 lined up and indicated according to the medical image informations stored in the medical image information database.

FIG. 13 is a diagram showing an example of the cross section cross section images on the cross sections A1, A2, A3 and A4 of the object shown in FIG. 12 lined up and indicated according to the medical image informations stored in the medical image information database 15.

As shown in FIG. 13, a tomographic image obtained at the head side A1 shows three tomograms, since both the arms portions are present, and each tomographic image of the body trunk portions A2, A3, and A4 shows one tomogram.

The pixel distribution histogram generating unit 10 detects pixel values at positions in each tomographic image as shown in FIG. 13 to generate a pixel distribution histogram.

Figure 14:
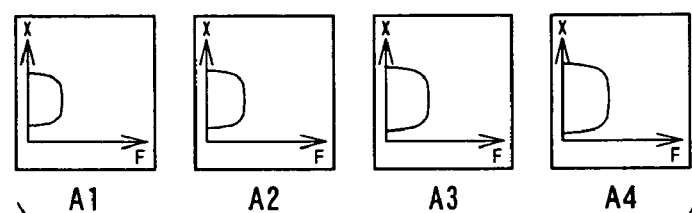
FIG. 14 is a diagram indicating pixel distribution histograms on the cross sections A1, A2, A3 and A4 of the object in FIG. 12 according to the direction of the X axis which is assumed to be the cross direction from the viewpoint of the object.
Figure 15:
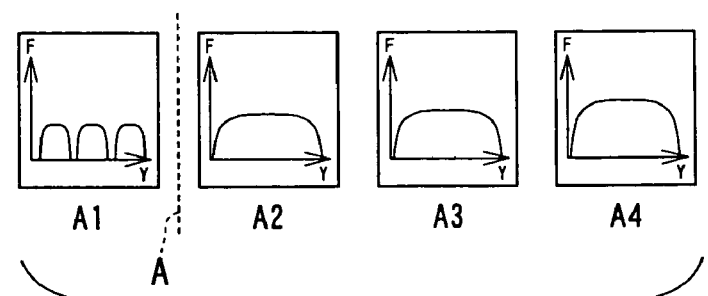
FIG. 15 is a diagram indicating pixel distribution histograms on the cross sections A1, A2, A3 and A4 of the object in FIG. 12 according to the direction of the Y axis which is assumed to be the horizontal direction from the viewpoint of the object.

FIG. 14 is a diagram indicating pixel distribution histograms on the cross sections A1, A2, A3 and A4 of the object in FIG. 12 according to the direction of the X axis which is assumed to be the cross direction from the viewpoint of the object. FIG. 15 is a diagram indicating pixel distribution histograms on the cross sections A1, A2, A3 and A4 of the object in FIG. 12 according to the direction of the Y axis which is assumed to be the horizontal direction from the viewpoint of the object.

FIG. 14 shows frequency distribution of pixels whose pixel values exceed a predetermined threshold according to the x-axis-direction, and FIG. 15 shows the frequency distribution of pixels whose pixel values exceed a predeterme threshold according to the y-axis-direction.

As shown in FIG. 14, the pixel distribution histogram in the x-axis-direction has a single region. In contrast, as shown in FIG. 15, the pixel distribution histogram in the y-axis-direction has three regions, since both the arm portions, other than the head portion, also exist in the corresponding tomographic image at the head side A1. Furthermore, each of the pixel distribution histogram in the y-axis-direction corresponding to each tomographic image of the trunk portion A2, A3, or A4 has a single region.

Thus, for example, when the number of regions within the pixel distribution histogram in the y-axis-direction is detected, it is possible to identify to which portion of the subject a tomographic image corresponds. Accordingly, when three regions exist in the pixel distribution histogram in the y-axis-direction, the pixel distribution histogram generating unit 10 determines that a corresponding tomographic image is a tomographic image for the head portion of the subject. When a single region exists in the pixel distribution histogram in the y-axis-direction, the pixel distribution histogram generating unit 10 determines that a corresponding tomographic image is a tomographic image for the chest portion of the subject. In order to allow the tomographic images to be sorted into a group for the head portion and a group for the chest portion, the pixel distribution histogram generating unit 10 sets the group border A between the tomographic images where the number of regions in the pixel distribution histogram in the y-axis-direction changes from one to three, i.e., between the tomographic image of the head portion and the tomographic image of the chest portion.

Figure 16:
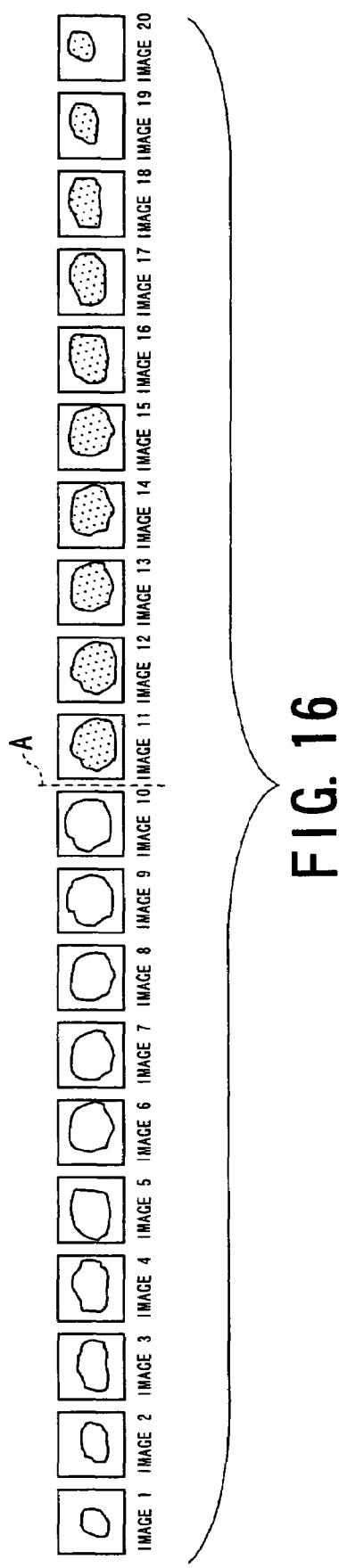
FIG. 16 is a diagram for explaining another example of the way to set a border A of the groups for the medical images according to pixel distributions of the medical images by the group information generating system shown in FIG. 1.

FIG. 16 is a diagram for explaining another example of the way to set a border A of the groups for the medical images according to pixel distributions of the medical images by the group information generating system 1 shown in FIG. 1.

FIG. 16 shows an example in which tomographic images of the subject's slice obtained by the go-and-reverse bed moving method after and before injection of the contrast medium are arranged in a time sequence order. That is, for example, a total of twenty tomographic images (image 1, image 2, . . . , image 20) of the entire body of the subject are arranged in a time sequence order with ten tomographic images thereof being obtained before injection of the contrast medium and the other ten tomographic images being obtained after injection of the contrast medium.

The ten tomographic images (image 1, image 2, . . . , image 10) before the contrast medium injection are imaged, for example, from the positive side of the body axis toward the negative side with respect to the body trunk of the subject, and change such that the size increases. On the other hand, the ten tomographic images (image 11, image 12, . . . , image 20) after the contrast medium injection are imaged, for example, from the negative side of the body axis toward the positive side with respect to the body trunk of the subject, and change such that the size decreases.

In order that tomographic images of the subject before the contrast medium injection and tomographic images of the subject after the contrast medium injection are sorted into groups different from each other, the pixel distribution histogram generating unit 10 determines maxima of the pixel distribution histograms for tomographic images in an arbitrary direction, for example, in the y-direction, and further detects a local maximal value when the maxima of the pixel distribution histograms are arranged in a time series. Then, the group border A is set between the tomographic images corresponding after and before the local maximal value of the maxima of the pixel distribution histograms, i.e., between the tomographic images corresponding after and before the bed moving direction changes.

In this manner, the group border A can be set by identifying a portion of the subject based on arbitrary information, such as the number of regions, the maximum values, the range, and the area in the pixel distribution histogram. The method for setting the group border A is preset.

The pixel distribution histogram generating unit 10 supplies the preset group border A to the adjustment group generating unit 11 or the group information generating unit 12 as border information.

Next, in step S3, the adjustment group generating unit 11 sets borders A' for creating an adjustment group to thereby generate adjustment group border information according to need.

When the group border A is automatically set based on the numeric data of the pixel distribution histograms of tomographic images, there is a risk in that the group border A is not appropriately set as intended, due to factors, such as error in the pixel distribution histograms. In some cases, it is desired that tomographic images that are determined to be adjacent to the group border A based on the threshold of the pixel values be provided with margins so that a certain number of tomographic images are sorted into the same group. Further, in some cases, it is desired that one or some tomographic images that are not required for diagnosis be excluded from a group. Accordingly, the borders A' for creating an adjustment group is automatically set by a predetermine method according to need, depending on the purpose of diagnosis and the application of data.

Figure 17:
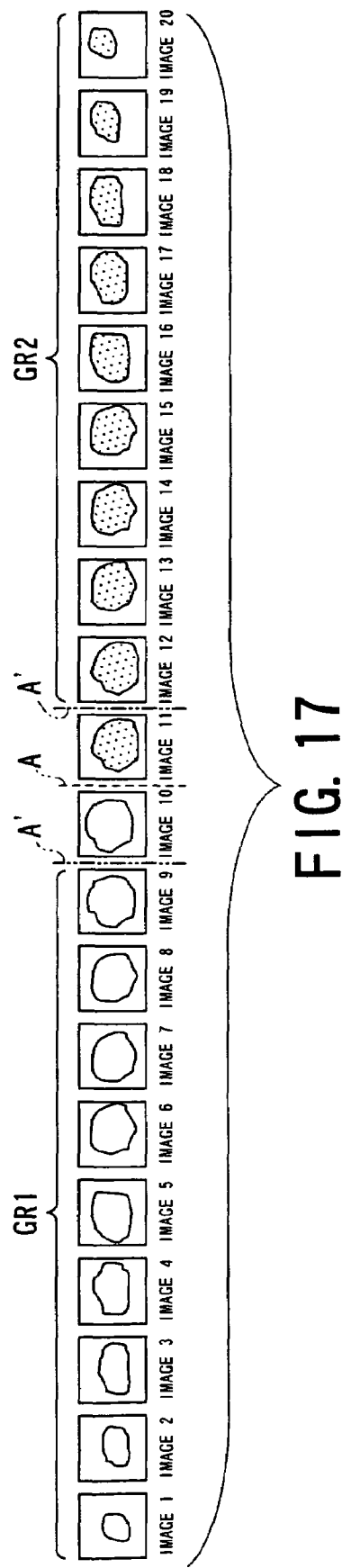
FIG. 17 is a diagram showing an example of the way to set borders A' for generating the adjustment groups to the medical images in FIG. 16.

FIG. 17 is a diagram showing an example of the way to set borders A' for generating the adjustment groups to the medical images in FIG. 16.

For example, as shown in FIG. 17, the adjustment group generating unit 11 automatically sets the adjustment-group borders A' such that two tomographic images that are adjacent to the group border A set by the pixel distribution histogram generating unit 10 are sorted into an adjustment group.

Next, in step S4, the group information generating unit 12 generates group information, based on the group border information and the adjustment group border information, and writes the generated group information to the group information database 16. During this process, the group information generating unit 12 sets, in the group information, the display order of medical images grouped into the same group, according to need. In the case of the medical images shown in FIG. 17, since the bed moving directions after and before the contrast medium injection are opposite to each other, the group information generating unit 12 sets the tomographic images that were imaged before the contrast medium injection and that are divided by the adjustment group border A' as group 1 so that the display order thereof is to be the time sequence order, and sets the tomographic images that were imaged after the contrast medium injection and that are divided by the adjustment group border A' as group 2 so that the display order thereof is to be the reverse order of time.

Next, in step S5, the group information revising unit 13 appropriately revises the group information stored in the group information database 16, according to need.

In step S6, the image indicating unit 14 supplies the image-indicating information, read from the medical image information database 15, to the monitor 5 in accordance with the group information, so that the tomographic images of the subject are displayed in a group on the monitor 5 in an aligned manner.

Figure 18:
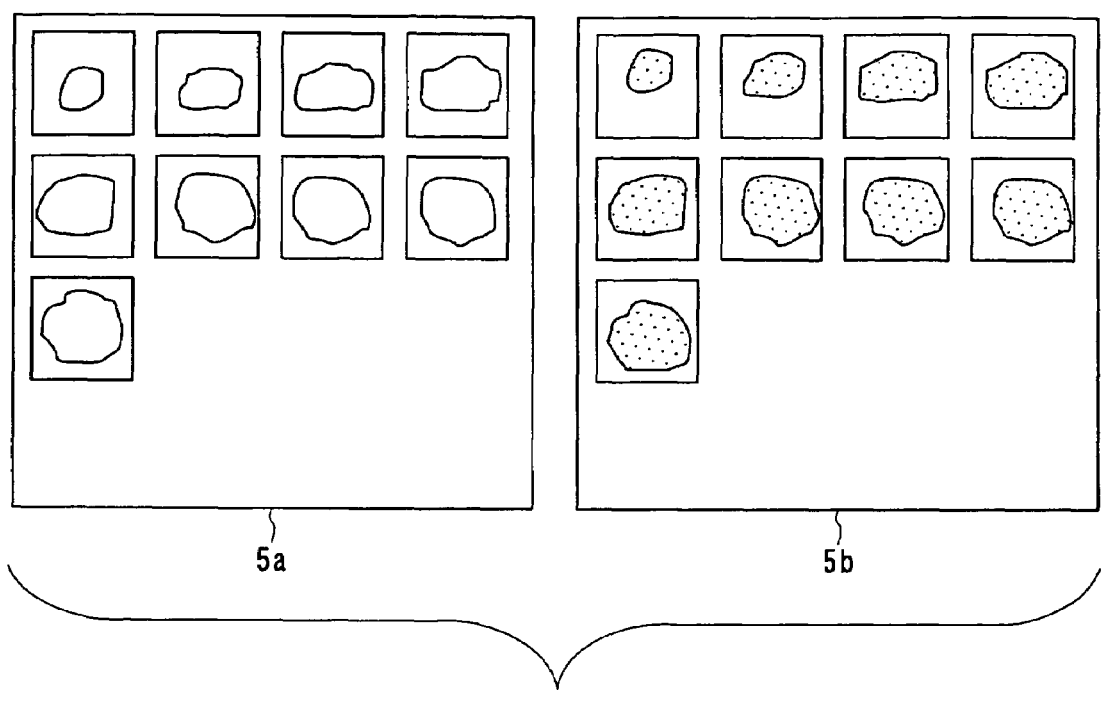
FIG. 18 is a diagram showing an example of the cross section images in FIG. 17 sorted into the groups and indicated on the monitor.

FIG. 18 is a diagram showing an example of the cross section images in FIG. 17 sorted into the groups and indicated on the monitor 5.

As shown in FIG. 18, of ten tomographic images (image 1, image 2, . . . , image 10) obtained before the contrast medium injection, nine tomographic images (image 1, image 2, . . . , image 9) sorted into group 1 are displayed on a common monitor 5*a* in an aligned manner in a time series. Of ten tomographic images (image 11, image 12, . . . , image 20) obtained after injection of the contrast medium, nine tomographic images (image 12, image 13, . . . , image 20) sorted into group 2 are displayed on another common monitor 5*b* in an aligned manner in reverse order of time.

Consequently, by referring to the appropriately-grouped tomographic images on the monitor 5, the user can readily interpret the images, can easily understand the flow of imaging of the medical images, and can easily perform 3-dimensional interpretation on the subject.

According to the group-information generating system 1 described above, it is possible to assume the imaging situation of a medical image and a imaged portion of a subject, based on the information, such as position information of the bed and pixel distribution, that is acquired from the medical image information. Further, the group-information generating system 1 can automatically generate group information for displaying multiple medical images acquired by multiple different modalities, in a group in an aligned manner, in accordance with the imaging situation of the medical images and a imaged portion of the subject. Thus, it is possible to perform comprehensive group management of medical images.

Since the group information is generated from common information contained in medical image information regardless of the kind or type of modality, a difference in image combinations in groups automatically created for respective modalities can be absorbed and medical images obtained by an arbitrary modality can be displayed in a group on an arbitrary image referring apparatus.

In addition, the creation of the adjustment group allows unnecessary medical images to be excluded from a group, allows the data size to be reduced, and allows the user to easily judge whether to keep or dispose medical images sorted into an adjustment group. Thus, even when there is a need to adjust a group border directly generated from the position information of the bed or pixel distribution, the creation of the adjustment group leads to automated creation of group information, thereby making it possible to reduce the user's work. Conversely, when the group information still needs to be adjusted even after the creation of the adjustment group, the group border can be revised such that the medical images are sorted into groups intended by the user, by using images for reference, such as scanogram data.

Some of the functions of the group-information generating system 1 may be omitted and a function that serves as an image referring apparatus, using the monitor 5 as an element, maybe provided.

Instead of providing the group information generating information 1 with the turn of data detecting unit 9 and the pixel distribution histogram generating unit 10 as the group-border information generating units, the group-information generating system 1 may be provided with a group-border information generating unit having another function.

For example, the group-information generating system 1 may be provided with a group-border information generating unit that generates group border information using predetermined data of incidental information included in the medical image information.

Figure 19:
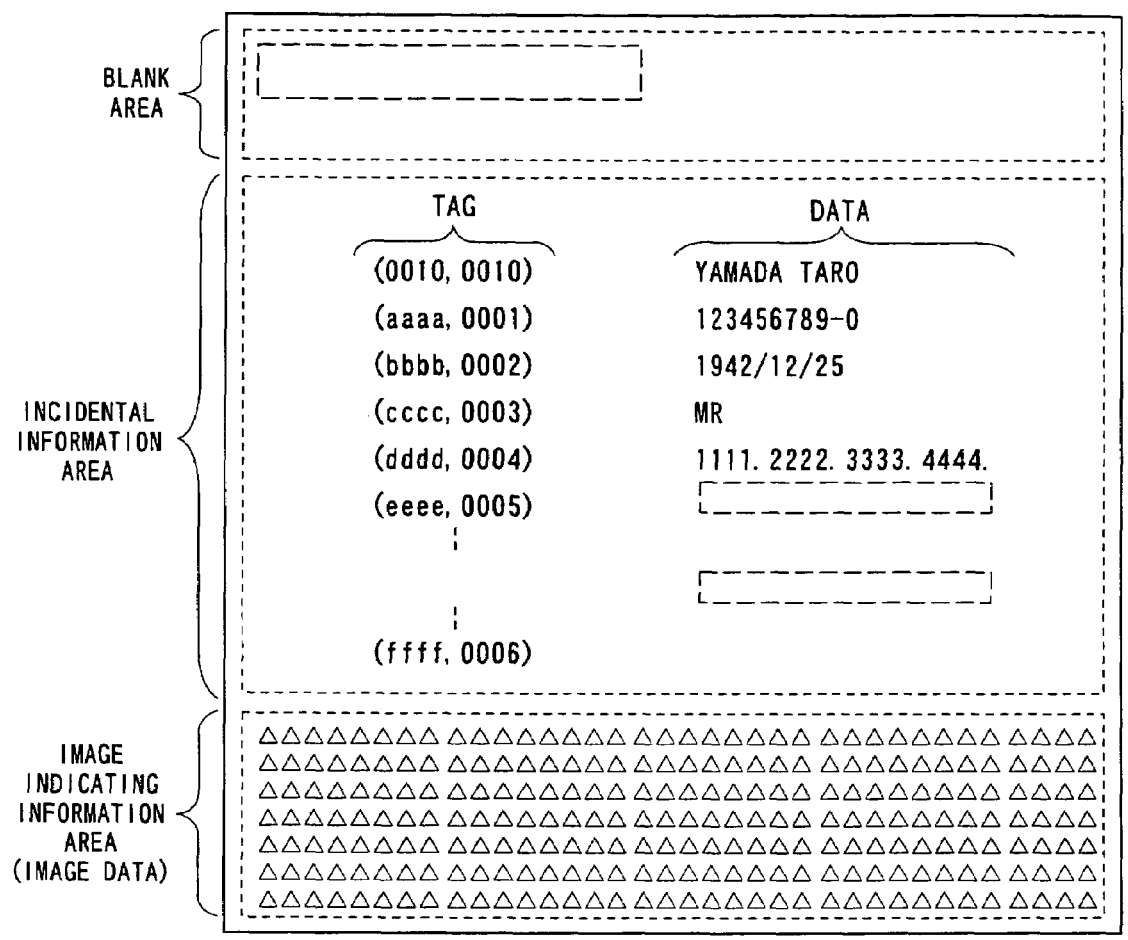
FIG. 19 is a diagram indicating an example of the incidental information used for generating the border informations of the group.

FIG. 19 is a diagram indicating an example of the incidental information used for generating the border informations of the groups.

As shown in FIG. 19, the medical image information has a blank area, an incidental information area, and an image-indicating information (image data) area. Incidental information is described in the incidental information area. The incidental information is constituted by multiple pieces of data and tags indicating what the respective pieces of data mean. Accordingly, specifying a tag of data indicating a desired content and referring to data that follows the specified tag can obtain intended data.

The incidental information typically includes data such as a patient's name, the patient's discernment information, the patient's birth data, the type of modality that imaged the corresponding image, the position information of the bed, discernment information of the image, an examination comment and so on. The incidental information can also include scan conditions, such as the use/non-use of a contrast medium; the value of tube current or tube voltage of an X-ray tube; and information indicating whether or not predetermined filtering has been performed on the image data.

FIG. 20 is a table indicating an example of a part of tags for CT images, which can be used for generating group-border information and descriptions of them in the incidental information of the medical image information shown in FIG. 19. FIG. 21 is a table indicating an example of a part of tags for MR images, which can be used for generating group-border information and descriptions of them in the incidental information of the medical image information shown in FIG. 19.

Referring to FIG. 20 and FIG. 21, Some data, having desired description, corresponded to tags can be included to the medical image information as data of the incidental information. Each of FIG. 20 and FIG. 21 shows an example of tags set up according to DICOM.

More specifically, in case that the medical image is a CT image, informations such as the bolus agents used as a contrast medium, the body part examined, the slice thickness, the tube voltage of the X-ray tube (KVP), bolus start time of the contrast medium, the X-ray tube current, the exposure of the X-ray, the convolution kernel of the CT images, the series number to which the CT image belongs, the image position of the patient and so on can be included in the incidental information with corresponding them to tags.

Similarly, in case that the medical image is a MR image, informations such as the bolus agents used as a contrast medium, the body part examined, the slice thickness, the repetition time, the echo time, the inversion time, the echo number(s), series instance UID (unique identifier), the acquisition number of the data, the image position of the patient and so on can be included in the incidental information with corresponding them to tags.

Furthermore, each tag is connected with a code indicating VR (Value Representation) of the data such as LO (Long String), SH (Short String), CS (Code String), DS (Decimal String for floating decimal mode), IS (Decimal String for integer mode), TM (Time), UI (unique identifier) and so on.

Thus, desired information obtained from the incidental information included in the medical image information by appointing tags setup like above-mentioned can be used for generating the border information of group.

Accordingly, for example, the group-border information generating unit may be configured so as to refers to a pre-specified tag to thereby detect the use/non-use of a contrast medium for each piece of medical image information and generate group border information in accordance with the use/non-use of a contrast medium.

When the group-border information generating unit refers to the pre-specified tag, not only the use/non-use of a contrast medium but also a desired single or multiple scan conditions, including a tube current value or a tube voltage value of an X-ray tube and information indicating whether predetermined filtering has been performed on the image data, can be obtained for each piece of medical image information. The group-information generating unit may also be configured to generate group border information in accordance with the obtained single scan condition or a combination of the multiple scan conditions. When the group-border information generating unit uses a tube current value or tube voltage value of an X-ray tube to generate group border information, it is possible to generate group border information based on whether or not the tube-current value, tube-voltage value, or the fluctuation range thereof, which are obtained from the incidental information, exceeds a predetermined threshold preset with respect to the tube current value, the tube voltage value, or the fluctuation range thereof.

What is claimed is:

1. A group information generating system comprising:
   a group border information generating unit configured to generate histograms of pixel values of plural images corresponding to mutually different cross sections based on a medical image information and generate a border information indicating at least one border of a group when medical images sorted into the group are to be indicated according to the histograms; and
   a group information generating unit configured to generate a group information according to the border information, the group information meaning a discernment information of the group to which an image indicating information included in the medical image information for indicating one of the medical images is belong.

2. A group information generating system according to claim 1,
   wherein the group border information generating unit is configured to generate the border information according to an incidental information included in the medical image information.

3. A group information generating system according to claim 1,
   wherein the group border information generating unit is configured to generate the border information according to a scan condition obtained from an incidental information included in the medical image information.

4. A group information generating system according to claim 1,
   wherein the group border information generating unit is configured to obtain a scan condition corresponding to predetermined tag information from an incidental information included in the medical image information by referring the predetermined tag information and generate the border information according to the scan condition.

5. A group information generating system according to claim 1,
   wherein the group border information generating unit is configured to detect whether contrast medium is used from an incidental information included in the medical image information and generate the border information according to the whether the contrast medium is used.

6. A group information generating system according to claim 1,
   wherein the group border information generating unit is configured to obtain a value of a tube electric current of X-ray tube from an incidental information included in the medical image information and generate the border information according to the value of the tube electric current.

7. A group information generating system according to claim 1,
   wherein the group border information generating unit is configured to detect a turn of position data of a bed from an incidental information included in the medical image information and generate the border information according to the turn.

8. A group information generating system according to claim 1, further comprising:
   a monitor;
   an image indicating unit configured to transmit the image indicating information to the monitor according to the group information to indicate the medical images sorted into the group and lined up on the monitor.

9. A group information generating system according to claim 1, further comprising:
   an adjustment group generating unit configured to generate an adjustment border information of an adjustment group according to the border information.

10. A group information generating system according to claim 1, further comprising:
    a group information revising unit configured to give a reference image information to a monitor to indicate a reference image and revise the group information according to an input from an input device.

11. A group information generating method comprising steps of:
    generating histograms of pixel values of plural images corresponding to mutually different cross sections based on a medical image information and generating a border information indicating at least one border of group when medical images sorted into the group are to be indicated according to the histograms; and
    generating a group information according to the border information, the group information meaning a discernment information of the group to which an image indicating information included in the medical image information for indicating one of the medical images is belong.

12. A group information generating method according to claim 11, wherein the border information is generated according to an incidental information included in the medical image information.

13. A group information generating method according to claim 11,
wherein the border information is generated according to a scan condition obtained from an incidental information included in the medical image information.

14. A group information generating method according to claim 11,
wherein a scan condition corresponding to predetermined tag information is obtained from an incidental information included in the medical image information by referring the predetermined tag information and the border information is generated according to the scan condition.

15. A group information generating method according to claim 11,
wherein whether contrast medium is used is detected from an incidental information included in the medical image information and the border information is generated according to the whether the contrast medium is used.

16. A group information generating method according to claim 11,
wherein a value of a tube electric current of X-ray tube is obtained from an incidental information included in the medical image information and the border information is generated according to the value of the tube electric current.

17. A group information generating method according to claim 11, further comprising:
generating an adjustment border information of an adjustment group according to the border information.

18. A group information generating method according to claim 11, further comprising:
giving a reference image information to a monitor to indicate a reference image and revising the group information according to an input from an input device.

* * * * *